United States Patent [19]

Robertson

[11] Patent Number: 4,582,831

[45] Date of Patent: Apr. 15, 1986

[54] ANTI-INFLAMMATORY POLYMORPHIC MONOETHANOLAMINE SALT OF N-(2-PYRIDYL)-2-METHYL-4-HYDROXY-2H-1,2-BENZOTHIAZINE-3-CARBOXAMIDE 1,1-DIOXIDE COMPOUND, COMPOSITION, AND METHOD OF USE THEREFOR

[75] Inventor: Robert L. Robertson, Waterford, Conn.

[73] Assignee: Pfizer Inc., New York, N.Y.

[21] Appl. No.: 672,028

[22] Filed: Nov. 16, 1984

[51] Int. Cl.$^4$ .................... A61K 31/54; C07D 279/02
[52] U.S. Cl. ...................................... 514/225; 544/49; 514/222
[58] Field of Search ................... 544/49; 514/222, 225

[56] References Cited

U.S. PATENT DOCUMENTS 3,591,584  7/1971  Lombardino ..................... 260/243
4,434,164  2/1984  Lombardino ..................... 424/246

OTHER PUBLICATIONS

J. G. Lombardino et al., "Potent Antiinflammatory N-Heterocyclic 3-Carboxamides of 4-Hydroxy-2-Methyl-2H-1,-2H-1,2-2-Benzothiazine 1,1-Dioxide", *Journal of Medicinal Chemistry*, vol. 16, No. 5, p. 493, (1973).

*Primary Examiner*—Henry R. Jiles
*Assistant Examiner*—J. G. Mullins
*Attorney, Agent, or Firm*—Charles J. Knuth; Peter C. Richardson

[57] ABSTRACT

A novel crystalline form of the monoethanolamine salt of N-(2-pyridyl)-2-methyl-4-hydroxy-2H-1,2-benzothiazine-3-carboxamide 1,1-dioxide has been prepared. This novel crystalline form is designated as polymorph I and is useful in therapy as a non-steroidal anti-arthritic agent. Methods for preparing this polymorph from readily available materials are provided.

3 Claims, 4 Drawing Figures

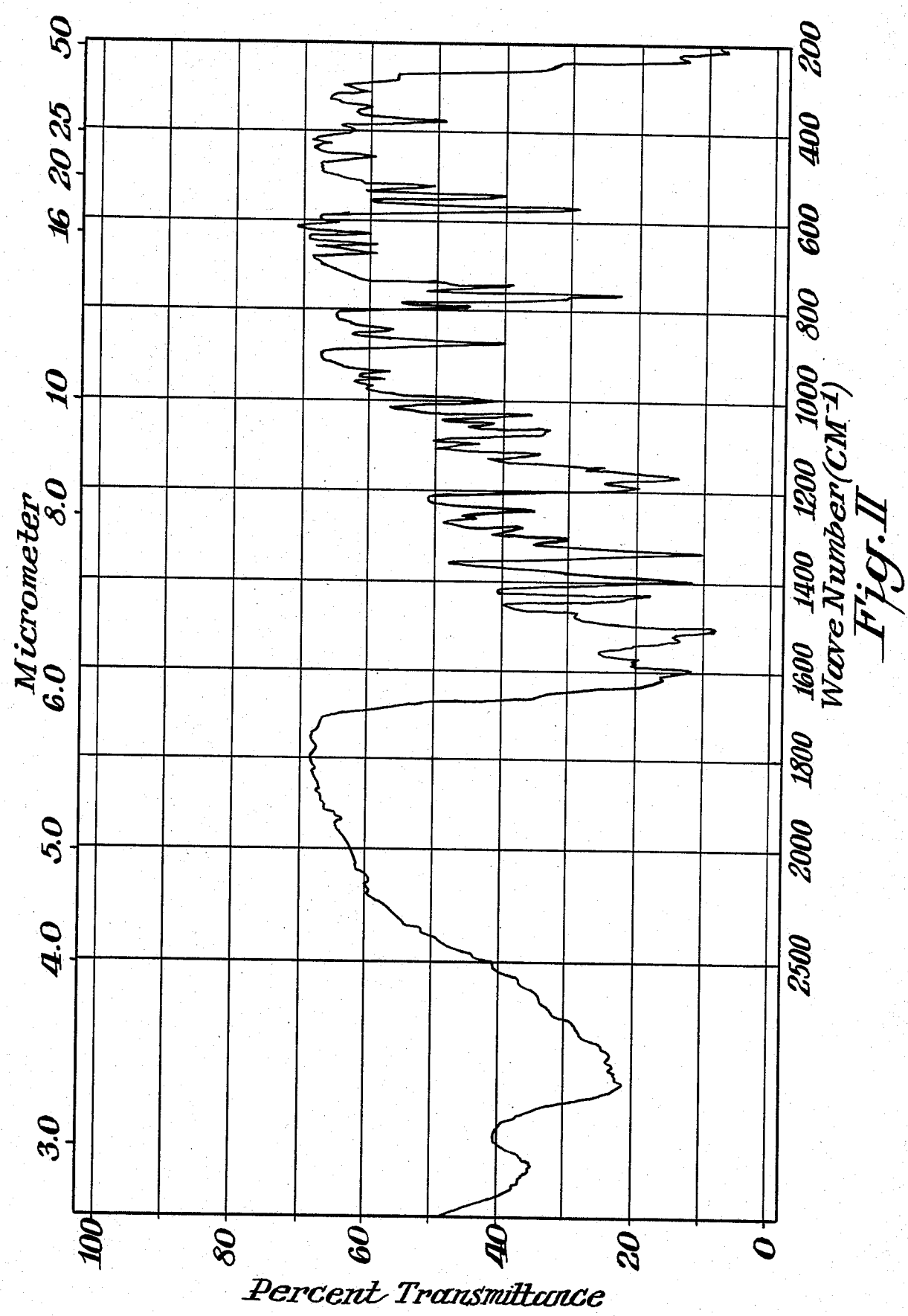
Fig. II

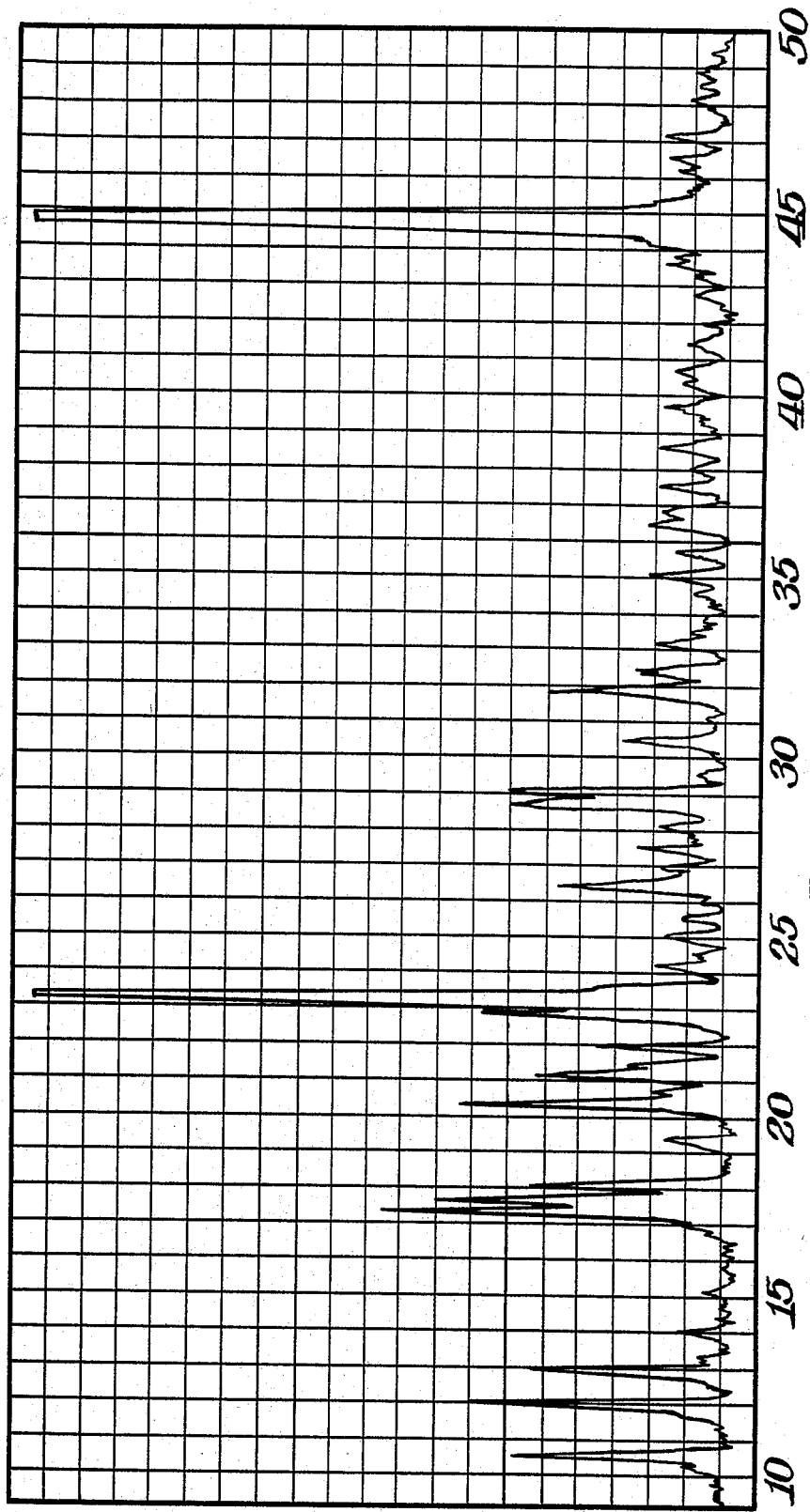
Fig. III

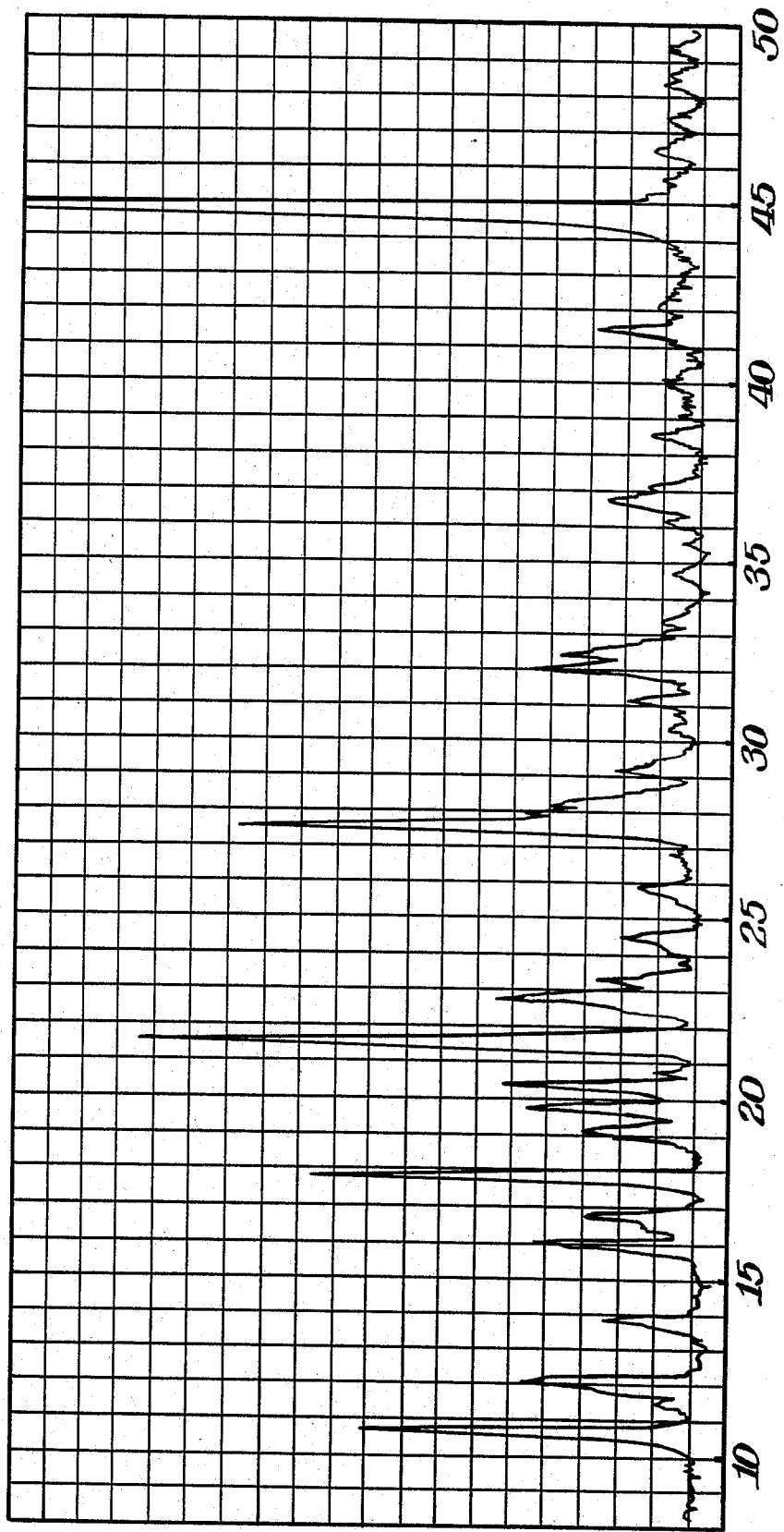
Fig. IV.

ANTI-INFLAMMATORY POLYMORPHIC MONOETHANOLAMINE SALT OF N-(2-PYRIDYL)-2-METHYL-4-HYDROXY-2H-1,2-BENZOTHIAZINE-3-CARBOXAMIDE 1,1-DIOXIDE COMPOUND, COMPOSITION, AND METHOD OF USE THEREFOR

BACKGROUND OF THE INVENTION

This invention relates to a new and useful form of an N-substituted 2-methyl-4-hydroxy-2H-1,2-benzothiazine-3-carboxamide 1,1-dioxide amine salt. More particularly, it is concerned with a novel crystalline form of the monoethanolamine salt of N-(2-pyridyl)-2-methyl-4-hydroxy-2H-1,2-benzothiazine-3-carboxamide 1,1-dioxide, which is of especial value in therapy in view of its unique combination of physical, chemical and biological properties.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including the new agent known as piroxicam. The latter substance is a member of a class of anti-inflammatory 4-hydroxy-2H-1,2-benzothiazine-3-carboxamide 1,1-dioxides described and claimed in U.S. Pat. No. 3,591,584 and is specifically, N-(2-pyridyl)-2-methyl-4-hydroxy-2H-1,2-benzothiazine-3-carboxamide 1,1-dioxide. In U.S. Pat. No. 4,434,164, there is specifically described and claimed the monoethanolamine salt of N-(2-pyridyl)-2-methyl-4-hydroxy-2H-1,2-benzothiazine-3-carboxamide 1,1-dioxide (piroxicam olamine), which is particularly valuable in pharmaceutical dosage forms as a non-steroidal therapeutic agent for the treatment of painful inflammatory conditions, such as those caused by rheumatoid arthritis, since it is a crystalline, non-hygroscopic, rapidly-dissolving solid with high water solubility. However, in the continuing search for still more improved anti-inflammatory agents, there is a definite need for anti-arthritic agents that possess an even higher degree of chemical stability. For instance, it is to be noted that the monoethanolamine salt product of aforesaid U.S. Pat. No. 4,434,164 formed a degradation product amounting to 0.3-0.6% per year when stored at 30° C. This degradation product will hereinafter be referred to as "the transient impurity" because it decomposes when dissolved in water or methanol.

SUMMARY OF THE INVENTION

In accordance with the present invention, it has now been found that a novel crystalline polymorph of the monoethanolamine salt of N-(2-pyridyl)-2-methyl-4-hydroxy-2H-1,2-benzothiazine-3-carboxamide 1,1-dioxide, hereinafter designated as polymorph I, is extremely useful as a non-steroidal therapeutic agent for alleviating painful inflammatory conditions, such as those caused by rheumatoid arthritis, for reasons that will hereinafter become readily apparent. This novel crystalline polymorph melts with decomposition at about 178°–181° C., and exhibits a characteristic X-ray powder diffraction pattern with characteristic peaks expressed in degrees 2θ at 10.6°, 12.1°, 13.0°, 17.4°, 17.6°, 18.1°, 19.3°, 20.4°, 21.1°, 21.9°, 26.4°, 28.7°, 29.0°, 30.4°, 31.9° and 32.5°; and is further characterized by the infrared absorption spectrum in potassium bromide having the following characteristic absorption bands expressed in reciprocal centimeters: 1620, 1595, 1570, 1530, 1510, 1435, 1400, 1315, 1300, 1287, 1250, 1235, 1180, 1165, 1150, 1112, 1090, 1060, 1010, 990, 975, 930, 870, 800, 770, 775, 735, 660, 650, 620, 565, 540, 510, 455, 400 and 365. The novel crystalline polymorph of this invention (viz., polymorph I) has a decided advantage over the other form of the drug earlier disclosed in U.S. Patent No. 4,434,164 (polymorph II) in that it is substantially more stable. It thus possesses important advantages in handling, storage and formulations, etc., in addition to possessing all the other advantages exhibited by the earlier form of the drug. Accordingly, the polymorph I form of the monoethanolamine salt of N-(2-pyridyl)-2-methyl-4-hydroxy-2H-1,2-benzothiazine-3-carboxamide 1,1-dioxide is most especially valuable as a non-steroidal therapeutic agent for the treatment of painful inflammatory conditions, such as those caused by rheumatoid arthritis, and is most especially adapted for use in a wide variety of pharmaceutical dosage forms, including those designed for oral, topical, rectal and parenteral administration.

BRIEF DESCRIPTION OF THE DRAWINGS

FIG. I is the infrared absorption spectrum of the polymorph I form of the monoethanolamine salt of N-(2-pyridyl)-2-methyl-4-hydroxy-2H-1,2-benzothiazine-3-carboxamide 1,1-dioxide in potassium bromide.

FIG. II is the infrared absorption spectrum of the polymorph II form of the monoethanolamine salt of N-2-pyridyl)-2-methyl-4-hydroxy-2H-1,2-benzothiazine-3carboxamide 1,1-dioxide in potassium bromide.

Figure 1:
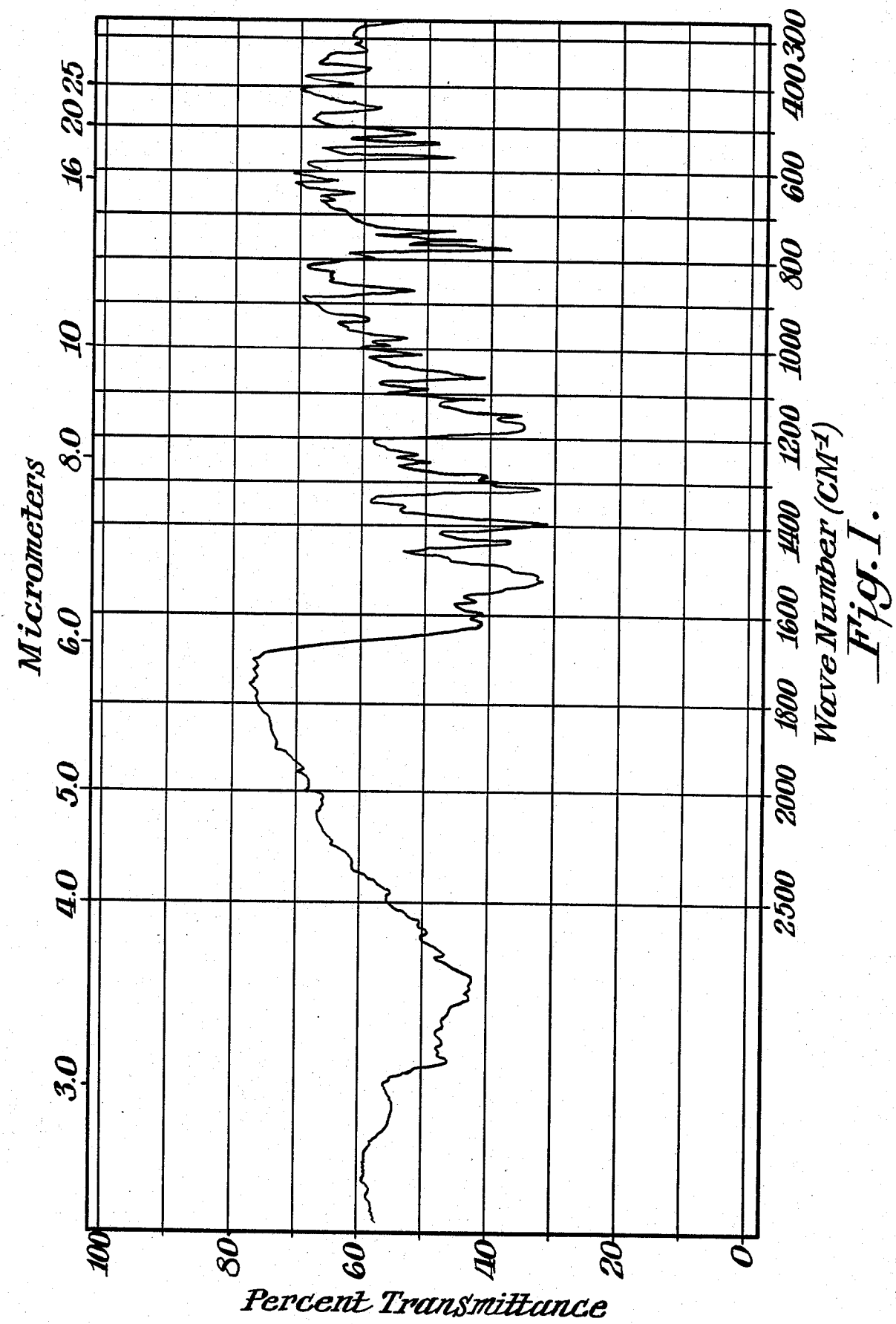

FIG. III is the characteristic X-ray powder diffractogram of the polymorph I form of the monoethanolamine salt of N-(2-pyridyl)-2-methyl-4-hydroxy-2H-1,2-benzothiazine-3-carboxamide 1,1-dioxide.

FIG. IV is the characteristic X-ray powder diffractogram of the polymorph II form of the monoethanolamine salt of N-(2-pyridyl)-2-methyl-4-hydroxy-2H-1,2-benzothiazine-3-carboxamide 1,1-dioxide.

DETAILED DESCRIPTION OF THE INVENTION

In accordance with the process employed for preparing the novel crystalline polymorph of this invention (viz., polymorph I), the monoethanolamine salt of N-(2-pyridyl)-2-methyl-4-hydroxy-2H-1,2-benzothiazine-3-carboxamide 1,1-dioxide, obtained in the form of polymorph II according to the procedure described by J. G. Lombardino in U.S. Pat. No. 4,434,164, is contacted with a suitable organic solvent for a sufficient period of time until formation of said desired polymorph I form is substantially complete. Upon completion of this step, the desired polymorph I form of the monoethanolamine salt of N-(2-pyridyl)-2-methyl-4-hydroxy-2H-1,2-benzothiazine-3-carboxamide 1,1-dioxide is readily recovered from the resultant slurry as a crystalline precipitate. In this way, polymorph II is completely converted to polymorph I.

In accordance with a more detailed consideration of the process of this invention, the conversion step is conducted in the presence of a polar, protic solvent or in a polar or non-polar, aprotic solvent at a temperature ranging from about 20° C. up to about the reflux temperature of the solvent, and preferably for from about 25° C. to about 80° C., for a period of about three to about 75 hours. Preferred polar, protic solvents for use in this connection include water and lower alkanols such as methanol, ethanol, isopropanol, n-butanol and isoamyl alcohol, while preferred polar and non-polar aprotic solvents include acetonitrile, acetone, methyl ethyl ketone, benzene, toluene and halogenated hydrocarbon solvents such as methylene chloride, chloroform, carbon tetrachloride, ethylene dichloride and s-tetrachloroethane, etc. The extent of polymorph I formation can be carefully monitored by isolating a sample of product during the course of the conversion and obtaining an infrared spectrum of the sample in potassium bromide. As previously indicated, polymorph I and polymorph II each have a characteristic infrared absorption spectrum.

An alternate and especially preferred embodiment of the process of this invention involves preparing polymorph I directly from N-(2-pyridyl)-2-methyl-4-hydroxy-2H-1,2-benzothiazine-3-carboxamide 1,1-dioxide and ethanolamine in an appropriate solvent of the type previously mentioned by seeding and then cooling slowly to 5° C. Examples 2 and 3 illustrate this method. The starting material required for this method, viz., N-(2-pyridyl)-2-methyl-4-hydroxy-2H-1,2-benzothiazine-3-carboxamide 1,1-dioxide (piroxicam) is described in U.S. Pat. No. 3,591,584 to J. G. Lombardino, as well as in the paper of J. G. Lombardino et al., appearing in the *Journal of Medicinal Chemistry*, Vol. 16, p. 493 (1973), including its overall synthesis from readily available organic materials. The ethanolamine reagent is, of course, a commercially available material.

The polymorph I form of the monoethanolamine salt of N-(2-pyridyl)-2-methyl-4-hydroxy-2H-1,2-benzothiazine-3-carboxamide 1,1-dioxide can be readily distinguished from the polymorph II form by means of infrared absorption spectroscopy. More particularly, the infrared spectra of polymorph I and polymorph II, when obtained by standard methods either as a potassium bromide (KBr) pellet or as a Nujol mull, provide a rapid and convenient method for characterizing said forms of the monoethanolamine salt. For instance, the characteristic infrared absorption spectrum of the polymorph I form of the monoethanolamine salt of N-(2-pyridyl)-2-methyl-4-hydroxy-2H-1,2-benzothiazine-3-carboxamide 1,1-dioxide is shown in FIG. I, while the infrared spectrum of FIG. II was obtained with a sample of the polymorph II form. The spectra are representative of those obtained on a Perkin-Elmer Model 21 recording infrared spectrophotometer employing potassium bromide pellets prepared by intimately grinding (viz., in a mortar and pestle) 1.0 mg. of the appropriate sample together with 300 mg. of potassium bromide. The mixture is then placed in a Perkin-Elmer die press model No. 1860025 and the die subjected to 15,000 p.s.i., while under vacuum for one minute. The characteristic infrared absorption bands which may be used for differentiating polymorph I from polymorph II are listed below in Table I as follows:

TABLE I

| Type of Product | Characteristic Bands | | |
|---|---|---|---|
| | $cm^{-1}$ | $\mu$ | comment |
| Polymorph I | 1250 | 8.00 | 1250 $cm^{-1}$ band stronger |
| | 1235 | 8.10 | |
| | 930 | 10.75 | singlet |
| | 770 | 12.00 | 770 $cm^{-1}$ band most intense |
| | 755 | 13.25 | |
| | 735 | 13.61 | |
| Polymorph II | 1250 | 8.00 | |
| | 1235 | 8.10 | 1235 $cm^{-1}$ band stronger |
| | 930 | 10.75 | doublet |

TABLE I-continued

| Type of Product | Characteristic Bands | | |
|---|---|---|---|
| | $cm^{-1}$ | $\mu$ | comment |
| | 775 | 12.90 | |
| | 765 | 13.07 | 765 $cm^{-1}$ band most intense |
| | 745 | 13.42 | |

The polymorph I form of the nonoethanolamine salt of N-(2-pyridyl)-2-methyl-4-hydroxy-2H-1,2-benzothiazine3-carboxamide 1,1-dioxide is also readily distinguished from the polymorph II form by means of X-ray diffractometry studies. The X-ray powder diffraction patterns are obtained on a Siemens diffractometer equipped with nickel-filtered copper radiation and a scintillation counter detector. In this particular method of analysis, the beam intensity as a function of the angle $2\theta$ is recorded at a scanning rate of 1° per minute. The characteristic X-ray powder diffractogram of polymorph I is shown in FIG. III, while the corresponding diffractogram for polymorph II is shown in FIG. IV. The peaks (expressed in "degrees $2\theta$") which may be used to distinguish one polymorphic form from another are summarized below in Table II as follows:

TABLE II

| Type of Product | Characteristic Peaks, degrees $2\Theta$ |
|---|---|
| Polymorph I | 17.4°, 17.6°, 18.1°, 29.0°, 30.4° |
| Polymorph II | 16.0°, 19.7°, 27.6°, 41.5° |

Still another method for distinguishing the polymorph I and polymorph II forms of the monoethanolamine salt of N-(2-pyridyl)-2-methyl-4-hydroxy-2H-1,2-benzothiazine-3-carboxamide 1,1-dioxide involves the use of differential scanning calorimetry (DSC) or differential thermal analysis (DTA). Samples (1-2 mg.) are analyzed on a Mettler DTA 2000 thermal analyzer at a range of 50-100 microvolts and at a heating rate of 20° C. per minute, with the samples being introduced at about 25° C. The results obtained with respect to the DSC are summarized below in Table III as follows:

TABLE III

| Type of Product | Summary of DSC Data on Samples |
|---|---|
| Polymorph I | Endotherm at ~190° C. |
| Polymorph II | Endotherm at ~177° C. |

Finally, stability studies have been carried out on bulk lots of the polymorph I and polymorph II forms of the monoethanolamine salt of N-(2-pyridyl)-2-methyl-4-hydroxy-2H-1,2-benzothiazine-3-carboxamide 1,1-dioxide. In these studies, samples are stored in clear glass bottles at 25° C., while exposing them to sunlight, and at 50° C. when placed in an oven. After such storage for six weeks and again at 12 weeks, the samples are observed for any visual or chemical changes. On this basis, all samples are found to have good chemical stability, but the stability exhibited by polymorph I is far superior to that of polymorph II. For instance, the polymorph I form showed no "transient impurity" after six weeks at 50° C., unlike polymorph II which exhibited some evidence of this degradation product even after a few days at room temperature as determined by high pressure liquid chromatography (HPLC) analysis.

From the above characterization studies on the two polymorphic forms of the monoethanolamine salt of N-(2-pyridyl)-2-methyl-4-hydroxy-2H-1,2-benzothiazine-3-carboxamide 1,1-dioxide, it is apparent that the polymorph I form has a distinct advantage over the polymorph II form in that it is extremely stable to storage conditions normally encountered, including exposure to sunlight. Also, it is readily and reproducibly prepared by the methods described herein.

As previously stated, the novel polymorph I form of the monoethanolamine salt of N-(2-pyridyl)-2-methyl-4-hydroxy-2H-1,2-benzothiazine-3-carboxamide 1,1-dioxide of the present invention is readily adapted to therapeutic use as an anti-arthritic agent. For instance, the polymorph I form of the aforesaid salt exhibits anti-inflammatory activity in the standard carrageenin-induced rat foot edema test [described by C. A. Winter et al., *Proc. Soc. Exp. Biol. Med.*, Vol 111, p. 544 (1962], where it was found to cause a substantial inhibition in swelling at the 33 mg./kg. dose level when given by the oral route. The herein described polymorph I form of the monoethanolamine salt of this invention exhibits all the advantages of the prior art polymorph II form, in addition to being far more stable as previously discussed. For example, even though N-(2-pyridyl)-2-methyl-4-hydroxy-2H-1,2-benzothiazine-3-carboxamide 1,1-dioxide (piroxicam) per se is very poorly-water soluble, the polymorph I form of the monoethanolamine salt of N-(2-pyridyl)-2-methyl-4-hydroxy-2H-1,2-benothiazine-3-carboxamide 1,1-dioxide is readily flash soluble (i.e., instantaneously soluble) in said solvent and, therefore, is more rapidly absorbed into the blood stream upon oral administration than the corresponding less soluble calcium salt or even the anhydrous sodium salt of said particular drug (both of which are prepared according to the procedure already set forth in U.S. Pat. No. 3,591,584). Additionally, this particular polymorph of the monoethanolamine salt affords a water-clear, conveniently formulated, stable aqueous solution even at very high concentration levels (>100 mg/ml.). This is in marked contrast to the tromethamine salt of N-(2-pyridyl)-2-methyl-4-hydroxy-2H-1,2-benzothiazine-3-carboxamide 1,1-dioxide and the corresponding triethanolamine salt which are both poorly water-soluble and the simple ammonium salt which is found to be highly unstable when subjected to drying conditions under vacuum. Moreover, the novel polymorph salt of this invention is a crystalline, non-hygroscopic solid which is readily isolated in a highly pure form. These particular properties, plus the stability factor, further facilitate the ease of bulk processing of said salt into finished pharmaceutical dosage forms that are especially adapted for use in either oral, topical, parenteral or rectal administration, etc.

The herein described polymorph I salt can be administered as an anti-arthritic agent by either of the routes previously indicated. In general, the polymorph salt of this invention will be administered in doses ranging from about 5.0 mg. up to about 1000 mg. per day, although variations will necessarily occur depending upon the weight and condition of the subject being treated and the particular route of administration chosen. A dosage level that is in the range of from about 0.08 mg. to about 16 mg. per kg of body weight per day is usually preferred, although variations may occur depending upon the individual response to said medicament, as well as on the type of pharmaceutical formulation chosen and the time intervals at which such administration is carried out. In some instances, dosage levels below the lower limit of the aforesaid range may be adequate, while in other cases higher levels may be employed, divided into several smaller doses for administration throughout the day.

The polymorph I salt of this invention may be administered alone or in combination with pharmaceutically acceptable carriers by the various routes previously indicated in a wide variety of different dosage forms, i.e., it may be combined with various pharmaceutically acceptable inert carriers in the form of tablets, capsules, soft and hard lozenges, troches, hard candies, powders, sprays, creams, salves, suppositories, jellies, pastes, lotions, ointments, aqueous solutions and suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the polymorph I salt of this invention is present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in hard geletin capsules; preferred materials also include lactose or milk sugar as well as high molecular weight polythylene glycols. When aqueous solutions and suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the polymorph I monoethanolamine salt in sesame or peanut oil or in aqueous propylene glycol or aqueous ethanol may be employed, as well as sterile aqueous solutions in distilled water. The aqueous solutions should be suitably buffered (pH>8) and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid polymorph I amine additon salt topically when treating inflammatory conditions of the skin or eye by way of creams, jellies, pastes, ointments, solutions and the like, in accordance with standard pharmaceutical practice.

The anti-inflammatory activity of the polymorph I salt of the present invention is demonstrated in the previously mentioned standard carrageenin-induced rat foot edema test. In this test, anti-inflammatory activity is determined as the percent inhibition of edema formation in the hind paw of male albino rats (weighing 150-190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. A compound is considered to be active under these conditions if the difference in response between drug-treated animals (six rats/group) and a control group receiving the vehicle alone is significant on comparison with the results afforded by standard compounds like acetylsalicyclic acid at 100 mg./kg. or phenylbutazone at 33 mg./kg., both by the oral route of administration.

PREPARATION A

Under speck-free conditions, there were dissolved 550 g. (1.66 moles) of N-(2-pyridyl)-2-methyl-4-hydroxy-2H-1, 2-benzothiazine-3-carboxamide 1,1-dioxide (prepared according to the procedure described by J. G. Lombardino in U.S. Pat. No. 3,591,584) in 6.6 liters of methylene chloride at 25°-30° C. The resulting solution was then filtered through fluted filter paper into a speck-free 12-liter, three-necked, round-bottomed flask equipped with stirrer and nitrogen atmosphere. At this point, stirring was commenced and 1.0 g. of the monoethanolamine salt of N-(2-pyridyl)-2-methyl-4-hydroxy-2H-1,2-benzothiazine-3-carboxamide 1,1-dioxide (prepared according to the procedure described by J. G. Lombardino in U.S. Pat. No. 4,434,164) was added to the solution as seeds. This was then followed by the introduction thereto of a solution consisting of 106.7 g. (1.75 moles) of ethanolamine dissolved in 1.1 liters of methylene chloride, which was added over a period of one hour. Upon completion of this step, the resultant slurry was granulated at the ambient temperature for a period of three hours and then filtered. The filtered crystals that were collected in this manner were then washed on the filter funnel (i.e., as the filter cake) with three-1000 ml. portions of methylene chloride at 23° C. and thereafter dried in a vacuum oven at 35° C. for a period of approximately 16 hours. In this way, there were ultimately obtained 643.1 g. of the pure crystalline monoethanolamine salt of N-(2-pyridyl)-2-methyl-4-hydroxy-2H-1,2-benzothiazine-3-carboxamide 1,1-dioxide, m.p. 170°-173° C. The net yield (642.1 g.) amounted to 98.6% of the theoretical value. After milling, the product weight 621 g. and was further dried in a vacuuum oven at 35°-38° C. for a period of 20 hours. The final melting point (m.p.) was 172°-173° C. This product was designated as polymorph II.

EXAMPLE 1

A 20 g. sample of the monoethanolamine salt of N-(2-pyridyl)-2-methyl-4-hydroxy-2H-1,2-benzothiazine-3-carboxamide 1,1-dioxide prepared in Preparation A (polymorph II) was dissolved in 400 ml. of anhydrous ethanol at reflux temperature. The resulting clear solution was then filtered through fluted filter paper into a 500 ml. speck-free Erlenmeyer flask. The filtered solution was then stirred via a magnetic stirrer at the ambient temperature for a period of 3.3 hours (temperature, 25° C.). At this point, the crystalline material which formed was collected by means of suction filtration, washed with anhydrous ethanol and dried in vacuo at 35° C. overnight (~16 hours) to give 16.9 g. (85%) of pure crystalline monoethanolamine salt of N-(2-pyridyl)-2-methyl-4-hydroxy-2H-1,2-benzothiazine-3-carboxamide 1,1-dioxide designated as polymorph I, m.p. 179°-180.5° C. Mixed melting point studies, mixed differential thermal analysis (DTA), infrared absorption spectra (IR) in potassium bromide (KBr) and X-ray powder diffraction analysis all confirmed the existence of the new polymorph.

Anal. Calcd. for $C_{17}H_{20}N_4O_5S$: C, 52.03; H, 5.14; N, 14.28. Found: C, 52.20; H, 5.39; N, 14.31.

EXAMPLE 2

In a 2-liter, four-necked, round-bottomed flask equipped with stirrer, steam bath and nitrogen atmosphere, there were placed 48.5 g. (0.146 mole) of N-(2-pyridyl)-2-methyl-4-hydroxy-2H-1,2-benzothiazine-3-carboxamide 1,1-dioxide (prepared as described in U.S. Pat. No. 3,591,584) and 1.3 liters of anhydrous ethanol. Stirring was commenced and the resultant slurry was slowly heated to 30°-35° C. At this point, a solution consisting of 9.4 g. (0.154 mole) of ethanolamine dissolved in 100 ml. of anhydrous ethanol was added to the mixture over a period of about ten seconds. Upon completion of this step, the resulting reaction mixture was further stirred at 35° C. for ca. 30 seconds to give a clear solution and was seeded at this point with crystals of polymorph I obtained from Example 1. This resulted in incipient crystallization of the desired product. The reaction mixture thus obtained was then stirred and slowly cooled in an ice-water bath to 5° C. (required approximately 15 minutes) and finally, further stirred as a slurry at 5° C. for a period of one hour prior to filtration. The recovered crystalline material was then washed (as a filter cake) with two-50 ml. portions of cold anhydrous ethanol and dried in vacuo at 35° C. over the week-end (~,72 hours) to afford 48.3 g. (84%) of pure crystalline monoethanolamine salt of N-(2-pyridyl)-2-methyl-4-hydroxy-2H-1,2-benzothiazine-3-carboxamide 1,1-dioxide in the form of polymorph I, m.p. 179°-180° C. The pure product was identical in every respect with the product of Example 1.

EXAMPLE 3

In a 3-liter, four-necked, round-bottomed flask equipped with stirrer, steam bath and nitrogen atmosphere, there were placed 100 g. (0.302 mole) of N-(2-pyridyl)-2-methyl-4-hydroxy-2H-1,2-benzothiazine-3-carboxamide 1,1-dioxide (prepared as described in U.S. Pat. No. 3,591,584) and 1.7 liters of isopropyl alcohol (isopropanol). Stirring was commenced and the resultant slurry was slowly heated to 30°-35° C. At this point, a solution consisting of 19.5 g. (0.319 mole) of ethanolamine dissolved in 100 ml. of isopropyl alcohol was added to the mixture in one portion. Upon completion of this step, the resulting reaction mixture was further stirred at 45° C. for ca. 60 seconds to give a clear solution and was seeded at this point (after heating ceased) with crystals of polymorph I obtained from Example 1. This resulted in incipient crystallization of the desired product. The reaction mixture thus obtained was then stirred at the ambient temperature for a period of approximately 15 minutes to give a good slurry and finally, cooled in an ice bath at 5° C. for a period of two hours just prior to filtration. The recovered crystalline material was then washed (as a filter cake) with three-50 ml. portions of isopropyl alcohol and dried in vacuo at 45° C. overnight (~16 hours) to afford 117 g. (99%) of the pure crystalline monoethanolamine salt of N-(2-pyridyl)-2-methyl-4-hydroxy-2H-1,2-benzothiazine-3-carboxamide 1,1-dioxide in the form of polymorph I, m.p. 179°-181° C. The pure product was identical in every respect with the product of Example 1.

A 10 g. sample of polymorph I (m.p. 179°-181° C.) was dissolved in 700 ml. of isopropyl alcohol (minimum amount) at reflux temperature. The resulting alcoholic solution was then filtered through fluted filter paper and stirred at the ambient temperature for a period of three hours (temperature, 25° C.). At this point, the crystalline material which formed was collected by means of suction filtration, washed with isopropyl alcohol and dried in vacuo at 45° C. overnight (~16 hours) to afford 8.2 g. of pure polymorph I, m.p. 178°–180° C.

A 10 g. sample of polymorph I (m.p. 179°–181° C.) was dissolved in 200 ml. of anhydrous ethanol (minimum amount) at reflux temperature. The resulting alcoholic solution was then filtered through fluted filter paper and stirred at the ambient temperature for a period of two hours (temperature, 30° C.). At this point, the crystalline material which formed was collected by means of suction filtration, washed with ethanol and dried in vacuo at 45° C. overnight (~16 hours) to again afford 7.5 g. of pure polymorph I, m.p. 178°–180° C.

EXAMPLE 4

In a 125 ml. one-necked, round-bottomed flask equipped with magnetic stirrer and glass stopper, there were placed 10 g. of the monoethanolamine salt of N-(2-pyridyl)-2-methyl-4-hydroxy-2H-1,2-benzothiazine-3-carboxamide 1,1-dioxide prepared in Preparation A (polymorph II), 1.0 g. of the same salt prepared as described in Example 3 (polymorph I) and 100 ml. of anhydrous ethanol. The resulting slurry was then stirred at the ambient temperature for a period of ca. 74 hours. At this point, the slurry was filtered and the desired product was subsequently collected by means of suction filtration and thereafter dried in vacuo at 45° C. until constant weight was achieved. In this way, there were ultimately obtained 9.9 g. (90%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C.

EXAMPLE 5

The procedure described in Example 4 was repeated except that isopropyl alcohol (100 ml.) was the solvent employed instead of ethanol and stirring was carried out for a period of ca. 73.5 hours. In this way, there were ultimately obtained 10.7 g. (97%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C.

EXAMPLE 6

The procedure described in Example 4 was repeated except that acetonitrile (100 ml.) was the solvent employed instead of ethanol and stirring was carried out for a period of ca. 73.5 hours. In this way, there were ultimately obtained 10.5 g. (95%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C.

EXAMPLE 7

The procedure described in Example 4 was repeated except that acetone (100 ml.) was the solvent employed instead of ethanol. In this way, there were ultimately obtained 7.1 g. (64%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C.

EXAMPLE 8

The procedure described in Example 4 was repeated except that methylene chloride (100 ml.) was the solvent employed instead of ethanol and stirring was carried out for a period of ca. 73.3 hours. In this way, there were ultimately obtained 10.1 g. (92%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C.

EXAMPLE 9

In a 125 ml. one-necked, round-bottomed flask equipped with magnetic stirrer and glass stopper, there were placed 10 g. of the monoethanolamine salt of N-(2-pyridyl)-2-methyl-4-hydroxy-2H-1,2-benzothiazine-3-carboxamide 1,1-dioxide prepared in Preparation A (polymorph II) and 100 ml. of methanol. The resulting mixture was then stirred at the ambient temperature for ca. 70.7 hours (complete solution was achieved after five minutes). At this point, the crystalline material which had already formed was subsequently collected by means of suction filtration and thereafter dried in vacuo at 45° C. until constant weight was achieved. In this way, there were ultimately obtained 3.9 g. (39%) of the pure crystalline monoethanolamine salt of N-(2-pyridyl)-2-methyl-4-hydroxy-2H-1,2-benzothiazine-3-carboxamide 1,1-dioxide entirely in the form of polymorph I, m.p. 178°–180° C. (the melting point of the polymorph II starting material was 170°–172° C. when determined side-by-side, heating at the rate of 1° per minute after 165° C.). Differential thermal analysis (DTA) and infrared absorption spectra (IR) in potassium bromide (KBr) confirmed that the product was identical in every respect with the product of Example 1 (i.e., polymorph I).

EXAMPLE 10

A tablet formulation is prepared by blending the following materials together in the proportions by weight specified below:

| | |
|---|---|
| The polymorph I form of the monoethanolamine salt of N—(2-pyridyl)-2-methyl-4-hydroxy-2H—1,2-benzothiazine-3-carboxamide 1,1-dioxide | 23.69 |
| Dicalcium phosphate, anhydrous | 113.37 |
| Polyvinylpyrrolidone | 50.00 |
| Modified pregelatinized starch, N.F. | 10.00 |
| Magnesium stearate | 2.65 |
| Sodium lauryl sulfate | 0.294 |

After the dried composition is thoroughly blended, tablets are punched from the resulting mixture, each tablet being of such a size that it contains 20 mg. of the active ingredient. Other tablets are also prepared in a similar fashion containing 5, 10 and 50 mg. of the active ingredient, respectively, by merely using the appropriate amount of the tablet blend in each case.

EXAMPLE 11

A dry solid pharmaceutical composition is prepared by combining the following materials together in the proportions by weight indicated below:

| | |
|---|---|
| The polymorph I form of the monoethanolamine salt of N—(2-pyridyl)-2-methyl-4-hydroxy-2H—1,2-benzothiazine-3-carboxamide 1,1-dioxide | 59.21 |

| | |
|---|---|
| -continued | |
| Dicalcium phosphate, anhydrous | 230.10 |
| Corn starch, U.S.P. | 32.50 |
| Sodium lauryl sulfate | 0.32 |
| Magnesium stearate | 2.87 |

The dried solid mixture so prepared is then thoroughly agitated so as to obtain a powdered product that is completely uniform in every respect. Hard gelatin (No.2) capsules containing the pharmaceutical composition are then prepared, employing a sufficient quantity of material in each instance so as to provide each capsule with 50 mg. of the active ingredient.

EXAMPLE 12

An aqueous propylene glycol solution containing the polymorph I form of the monoethanolamine salt of N-(2-pyridyl)-2-methyl-4-hydroxy-2H-1,2-benzothiazine-3-carboxamide 1,1-dioxide is prepared by dissolving the latter compound in propylene glycol-water (1:4 by weight) containing 1% by weight of trisodium phosphate and adjusted to an apparent pH of 8.0. The amount of compound employed is such that the resulting solution contains 5 mg. of the active ingredient per each ml. of solution. The solution is then sterilized by means of filtration through a 0.2 μm pore size cellulose membrane. The sterile aqueous propylene glycol solution so obtained is then suitable for intramuscular administration to animals.

EXAMPLE 13

An aqueous injectable solution is prepared by first intimately admixing one part by weight of the polymorph I form of the monoethanolamine salt of N-(2-pyridyl)-2-methyl-4-hydroxy-2H-1,2-benzothiazine-3-carboxamide 1,1-dioxide with 2.5 parts by weight of disodium phosphate with the aid of a mortar and pestle. The ground dry mixture so obtained is then sterilized with ethylene oxide and thereafter aseptically placed into vials and sealed. For purposes of intravenous administration, a sufficient amount of distilled water is added to each of the filled vials before use so as to ultimately provide a solution which contains 10 mg. of the active ingredient per each ml. of injectable solution.

EXAMPLE 14

A tablet formulation is prepared by blending the following materials together in the proportions by weight specified below:

| | |
|---|---|
| The polymorph I form of the monoethanolamine salt of N—(2-pyridyl)-2-methyl-4-hydroxy-2H—1,2-benzo-thiazine-3-carboxamide 1,1-dioxide | 23.92 |
| | 23.92 |
| Microcrystalline cellulose | 311.03 |
| Modified pregelatinized starch, N.F | 84.00 |
| Magnesium stearate | 0.945 |
| Sodium lauryl sulfate | 0.105 |

After the dried composition is thoroughly blended, tablets are punched from the resulting mixture, each tablet being of such a size that it contains 20 mg. of the active ingredient. Other tablets are also prepared in a similar fashion containing 5, 10 and 50 mg. of the active ingredient, respectively, by merely using the appropriate amount of the tablet blend in each case.

I claim:

1. The polymorph of the monoethanolamine salt of N-(2-pyridyl)-2-methyl-4-hydroxy-2H-1,2-benzothiazine3-carboxamide 1,1-dioxide which melts with decomposition at about 178°–181° C.; exhibits a characteristic X-ray powder diffraction pattern with characteristic peaks expressed in degrees $2\theta$ at 10.6°, 12.1°, 13.0°, 17.4°, 17.6°, 18.1°, 19.3°, 20.4°, 21.1°, 21.9°, 26.4°, 28.7°, 29.0°, 30.4°, 31.9° and 32.5°; and is further characterized by the infrared absorption spectrum in potassium bromide having the following characteristic absorption bands expressed in reciprocal centimeters: 1620, 1595, 1570, 1530, 1510, 1435, 1400, 1315, 1300, 1287, 1250, 1235, 1180, 1165, 1150, 1112, 1090, 1060, 1010, 990, 975, 930, 870, 800, 770, 755, 735, 660, 650, 620, 565, 540, 510, 455, 400 and 365.

2. An anti-arthritic composition comprising a pharmaceutically acceptable carrier and an effective anti-arthritic amount of a compound as claimed in claim 1.

3. A method for treating arthritic conditions in a warm-blooded animal, which comprises administering to said animal an effective anti-arthritic amount of a compound as claimed in claim 1.

* * * * *